United States Patent
Furuhata et al.

(10) Patent No.: US 7,828,754 B2
(45) Date of Patent: Nov. 9, 2010

(54) ULTRASONIC CEREBRAL INFARCTION THERAPEUTIC APPARATUS

(76) Inventors: Hiroshi Furuhata, 14-3-501, Kami-hiruta, Kasukabe-shi (JP) 344-0046; Toshiaki Abe, 3-16-1, Kohinata, Bunkyou-Ku, Tokyo (JP) 112-0006; Yuichi Murayama, #207, 3-28-17, Todoroki, Setagaya-Ku, Tokyo (JP) 158-0082; Takayuki Saguchi, Atago Green Hills Forest Tower, #403, 2-3-1, Atago, Minato-Ku, Tokyo (JP) 105-0002; Toshihiro Ishibashi, 1868-2-405, Ohfuna, Kamakura-Shi (JP) 247-0056

( * ) Notice: Subject to any disclaimer, the term of this patent is extended or adjusted under 35 U.S.C. 154(b) by 936 days.

(21) Appl. No.: 11/630,370
(22) PCT Filed: Mar. 18, 2005
(86) PCT No.: PCT/JP2005/005595
§ 371 (c)(1),
(2), (4) Date: Dec. 21, 2006
(87) PCT Pub. No.: WO2005/122933
PCT Pub. Date: Dec. 29, 2005

(65) Prior Publication Data
US 2009/0099482 A1    Apr. 16, 2009

(30) Foreign Application Priority Data
Jun. 21, 2004    (JP) ............................. 2004-182323

(51) Int. Cl.
*A61H 1/00* (2006.01)
(52) U.S. Cl. .......................................... 601/2; 600/439
(58) Field of Classification Search ................ 600/437, 600/439, 587; 601/2–4; 604/22
See application file for complete search history.

(56) References Cited

U.S. PATENT DOCUMENTS

| 5,295,487 A | 3/1994 | Saitoh et al. |
| 5,313,944 A | 5/1994 | Crowley et al. |
| 2004/0054282 A1 | 3/2004 | Aubry et al. |
| 2004/0138563 A1* | 7/2004 | Moehring et al. ............ 600/439 |
| 2006/0173321 A1* | 8/2006 | Kubota et al. ................ 600/439 |
| 2008/0262350 A1* | 10/2008 | Unger ......................... 600/439 |

FOREIGN PATENT DOCUMENTS

| JP | 57-193199 | 11/1982 |
| JP | 2003-325516 | 11/2003 |
| JP | 2004-024668 | 1/2004 |
| JP | 2004-120320 | 4/2004 |
| JP | 2004-154205 | 6/2004 |
| WO | 99/16360 A1 | 4/1999 |
| WO | 01/32258 A2 | 5/2001 |
| WO | 01/58337 A2 | 8/2001 |

OTHER PUBLICATIONS

English version of International Search Report dated Apr. 12, 2005.

* cited by examiner

*Primary Examiner*—Brian Casler
*Assistant Examiner*—Amanda Lauritzen
(74) *Attorney, Agent, or Firm*—Buchanan Ingersoll & Rooney PC

(57) ABSTRACT

An ultrasonic cerebral infarction therapeutic apparatus that does not produce side effects of destruction of brain cells, occurrence of intracerebral hemorrhage, destruction of nerve cells, etc. by avoiding formation of a standing wave by interference between an irradiated beam of an ultrasonic wave irradiated to the inside of the cranium and its reflected beam. An ultrasonic probe cap is constructed by arranging a plurality of laminated small transducers each made up of a PVDF film, a PZT ceramic, or the like in a mosaic-like pattern or in other form on the inside of the cap and one or more transducers are selected and activated according to a thrombus position. As a high frequency for actuating a transducer, a continuous sinusoidal wave, a burst wave, or a pulse wave shall be used so that no standing wave may be produced inside the cranium.

13 Claims, 10 Drawing Sheets

ULTRASONIC CEREBRAL INFARCTION THERAPEUTIC APPARATUS

FIELD OF THE INVENTION

This invention relates to an ultrasonic cerebral infarction therapeutic apparatus, and more specifically, to an ultrasonic cerebral infarction therapeutic apparatus that dissolves thrombus by irradiating an ultrasonic wave onto an embolic site of a cerebral infarction patient.

BACKGROUND OF THE INVENTION

For medical therapy of cerebral infarction (ischemic stroke), solving thrombus that caused cerebral infarction as early in the stage as possible after crisis is considered to be the most effective first selection. It is widely accepted that the sooner the restart of blood flow by dissolving the thrombus, the higher the effect of therapy becomes and the less the subsequent sequelae (dysphasia, paralysis, etc.) become.

As thrombolytic agents, urokinase (UK), streptokinase (SK), tissue plasminogen activator (TPA) having high thrombus affinity, etc. are used to dissolve thrombus. It is considered effective to apply such a thrombolytic agent within three hours after the crisis, and results of the therapy to patients show that improvement of symptoms by 30 to 40% has been observed by neurological evaluation at three months after the crisis.

Currently, improvement researches of the therapeutic technique by thrombolysis are being carried out principally in two directions below. The first improvement research of the therapeutic technique aims at improvement of a thrombolysis effect in a therapeutic time window that means a stage when a curative effect is expectable, namely, shortening of a thrombolysis time and restoration from penumbra (a state in which cerebral nerve cells are under ischemia). The second improvement research of the therapeutic technique aims at protecting cerebral nerve cells and further extending a time of the therapeutic time.

As a method for enhancing the thrombolysis effect by a thrombolytic agent, shortening a thrombolysis time, shortening a time from the crisis to recanalization of blood, and further reducing a dose of the thrombolytic agent from intravenous infusion by drip, there is proposed a method for promoting thrombolysis by irradiating the ultrasonic wave onto the embolic site (a portion in which thrombus occurred) and utilizing its ultrasonic energy.

As the thrombo-lysis method using the ultrasonic wave together, the following two methods have been proposed. The catheter ultrasonic irradiation method in which a catheter with an ultrasonic transducer on its point is inserted into blood vessel and the ultrasonic wave is irradiated onto a vicinity of the embolic site or across the embolic site, and the transcranial ultrasonic irradiation method in which the ultrasonic wave is irradiated toward the embolic site from the surface of the human body. The latter method includes a method that was applied by the present applicant and laid open as Japanese Laid Open Patent Publication No. 2004-024668.

It is found that the catheter ultrasonic irradiation method described above causes the following inconveniences in the case of applying it to actual therapy.

The first point is that in order to insert a catheter near the embolic site in a percutaneous transluminal manner, it is necessary to perform angiography by the X-ray contrastradiography or the digital subtraction angiography (DSA) and check an insertion status of the catheter. However, such a large-sized image display is not widely spread, there is a limit in applying these methods to patients.

The second point is that the ultrasonic transducer attached on the point of a catheter has low electroacoustic conversion efficiency and is easy to generate heat, and therefore has a high risk of promoting blood coagulation.

The third point is that, in the case where thrombus occurs in a peripheral vessel system, not in a main vessel system, the ultrasonic transducer provided on the point of the catheter cannot reach to targeted thrombus.

The fourth point is that, when targeted thrombus could be dissolved, if its fragment will flow into a peripheral vessel system and another thrombus will be generated in the peripheral vessel system, there will be no countermeasure.

The fifth point is that, since diagnostic and monitoring ultrasonic beams that have no therapeutic effects at all are simultaneously irradiated onto an ischemic area (infarction area) of a peripheral vessel system distal to the embolic site, side effects thereby are predictable.

On the other hand, the latter, the transcranial ultrasonic irradiation method does not produce the above-mentioned first to third points of inconveniences that are considered disadvantages of the catheter ultrasonic irradiation method described above, and so these disadvantages are solved.

However, it has become clear that the transcranial ultrasonic irradiation method produces following sixth and seventh points of inconveniences as will be described below.

The sixth point is that, although a low-frequency ultrasonic wave easily passes through the cranium, an ultrasonic beam irradiated into the cranium from the outside through one side thereof is reflected on the internal surface of the cranial bone on the other side, and the irradiated beam and the reflected beam interfere with each other to produce an acoustic resonant state inside the cranium, causing a temperature rise of the brain tissue.

The seventh point is that an ultrasonic beam irradiated into the inside of the cranium and a beam reflected on the internal surface of the cranial bone on the other side interfere with each other to produce a standing wave, and accordingly there is the possibility of generating an area where acoustic intensity increases abnormally at a spot inside the cranium, namely the so-called hot spot, which gives rise to risks of destruction of brain cells, occurrence of intracerebral hemorrhage, destruction of nerve tissue, etc.

Especially, the above-mentioned seventh point is a fatal side effect, that is, it is considered that occurrence of intracerebral hemorrhage results from a standing wave of the ultrasonic wave irradiated into the cranium.

SUMMARY OF THE INVENTION

This invention is to provide an ultrasonic cerebral infarction therapeutic apparatus that dissolves thrombus by irradiating an ultrasonic wave onto a thrombolic site of the cerebral blood vessel inside the cranium through it. To be concrete, the ultrasonic cerebral infarction therapeutic apparatus dissolves the thrombus by selecting an ultrasonic transducer from among one or a plurality of ultrasonic transducers arranged so as to cover a part or the whole of the head of a patient under therapy, activating it with a high frequency signal, and thereby irradiating the ultrasonic wave onto the embolic site that is a target of therapy.

Only an ultrasonic transducer suitable to irradiate the ultrasonic wave onto the embolic site of the head of the patient under therapy is selected and activated, and a frequency and a duration of the high frequency signal for activating the ultrasonic transducer is properly selected.

Since this scheme prevents the ultrasonic wave beam irradiated into the cranium and its reflected beam from interfering with each other to produce an acoustic resonant state inside the cranium, and prevents the irradiated ultrasonic wave beam and the reflected beam from interfering with each other to produce a standing wave, risks of destruction of brain cells, occurrence of intracerebral hemorrhage, destruction of nerve tissue, etc. are eliminated.

Moreover, since the apparatus has a structure of suitably cooling the head and the ultrasonic transducers from the outside, there is also no risk of causing a temperature rise in the brain tissue.

DETAILED DESCRIPTION OF THE PREFERRED EMBODIMENTS

Figure 1:
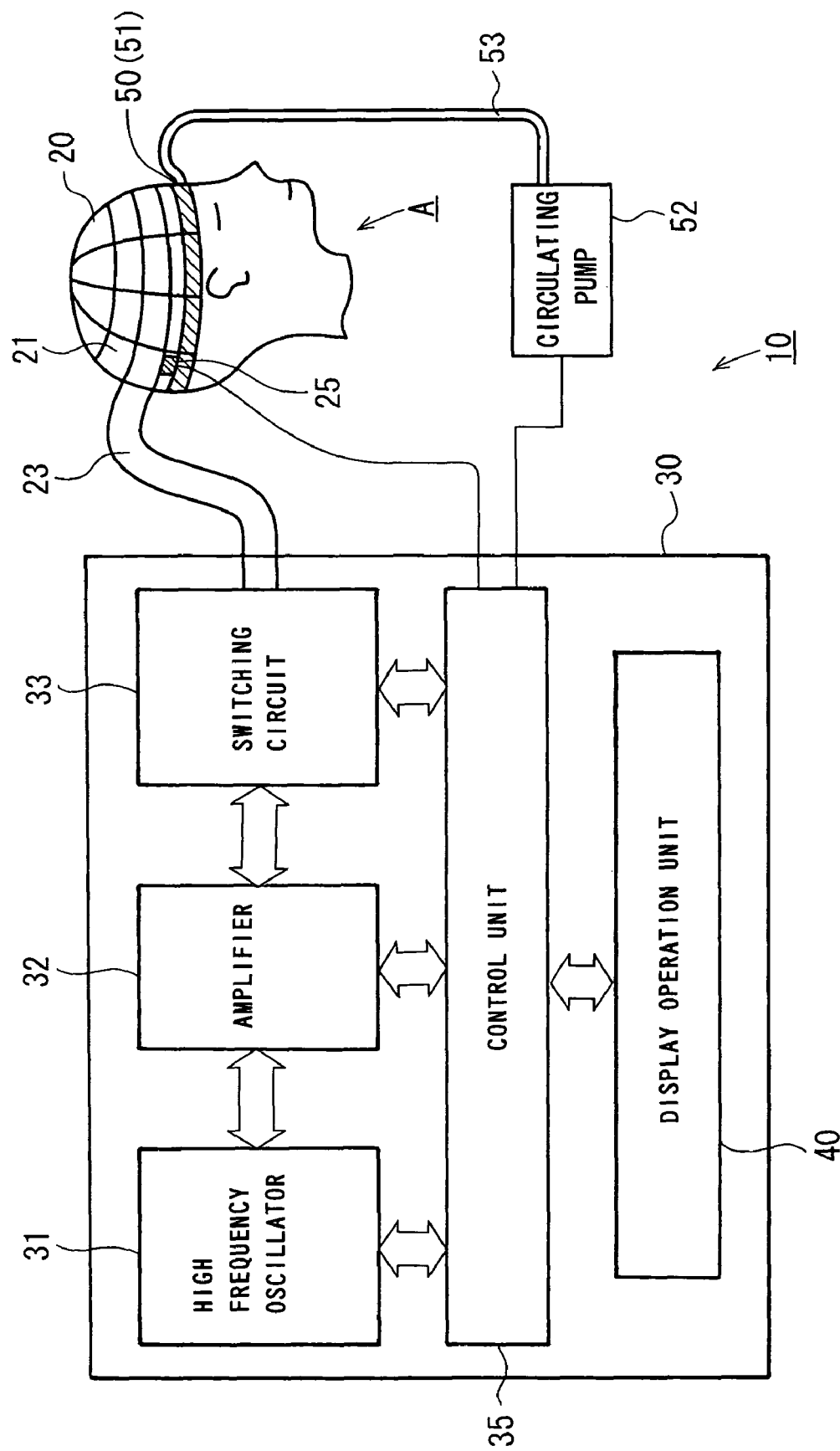
FIG. 1 is a diagram explaining a basic concept of an ultrasonic cerebral infarction therapeutic apparatus.

Hereafter, embodiments of this invention will be described. FIG. 1 is a diagram explaining a basic concept of an ultrasonic cerebral infarction therapeutic apparatus. An ultrasonic cerebral infarction therapeutic apparatus 10 consists of an ultrasonic irradiation device 20 equipped with a plurality of ultrasonic transducers each for irradiating an ultrasonic wave to the head of a patient under therapy A, a control device 30, and a cooling device 50 for cooling the head of the patient under therapy A and the ultrasonic transducers.

The control device 30 has a high frequency oscillator 31 for outputting a high frequency current for activating the ultrasonic transducer, an amplifier 32, a switching circuit 33 for selecting the ultrasonic transducer to be excited and supplying it with the high frequency current, a control unit 35 for setting up a drive frequency, an intensity, a driving time of the ultrasonic transducer, and a display operation unit 40, and controls the whole apparatus.

In the construction shown in FIG. 1, the cooling device 50 is made up of a cooling jacket 51 to which cold water is supplied from a circulating pump 52. Moreover, a temperature sensor 25 is attached to the ultrasonic irradiation device 20.

First, the ultrasonic irradiation device 20 will be explained. This invention aims at an ultrasonic irradiation device that can bring its ultrasonic transducers into tight contact with a part or the whole of the head of the patient under therapy A. As a first embodiment, an ultrasonic probe cap 20A is proposed; as a second embodiment, an ultrasonic probe pad 20B is proposed.

First, the ultrasonic probe cap 20A of the first embodiment will be explained. The ultrasonic probe cap 20A is a cap that is made up of a polyvinylidene fluoride (PVDF) film, as a row material, in the form capable of being brought into tight contact with the head and having flexibility. Although PVDF is a material that has an electromechanical transfer characteristic (piezoelectric characteristic), the efficient drive frequency is determined by the thickness of the film; therefore, in order to match the drive frequency with a comparatively low frequency being used in this embodiment, one that is made by laminating plural sheets of the films is desired.

However, in the case of a lamination of the films, it becomes difficult to bring it into tight contact with the head because of loss of the flexibility. Besides, it is necessary to configure the film so as to irradiate onto only the embolic site where thrombus occurred and so as not to irradiate the ultrasonic wave onto other sites. If the whole ultrasonic probe cap 20A is constructed with a single piece of a film lamination, the whole cap acts as an ultrasonic transducer. Since it is impossible to select and activate a specific portion of the cap as an ultrasonic transducer, it is not suitable.

In the first embodiment, the ultrasonic probe cap 20A is constructed by arranging one or a plurality of ultrasonic transducers 21 each made up of a necessary number of the PVDF films laminated together according to the drive frequency on the inside of the cap. The ultrasonic transducer 21 is constructed by forming positive and negative electrodes on both sides of a PVDF film by means of vapor deposition etc. and laminating a necessary number of the PVDF films according to the drive frequency.

Figure 2:
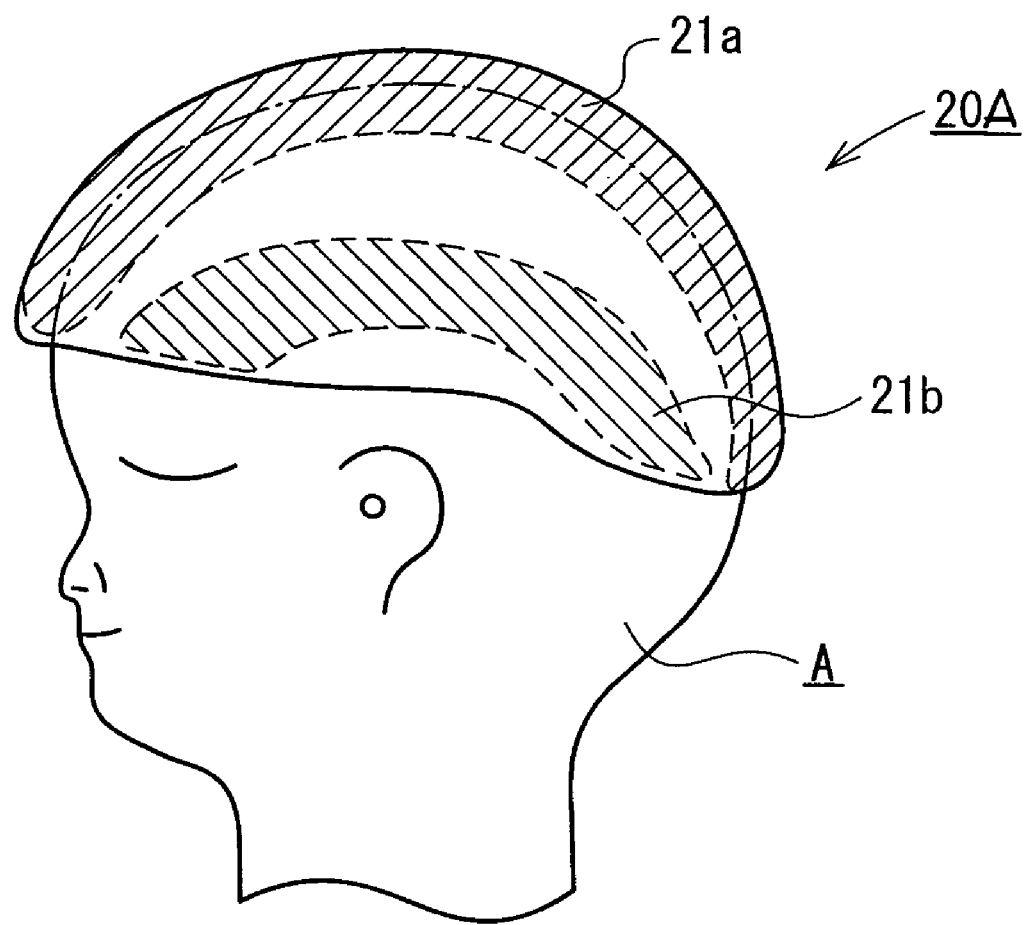
FIG. 2 is a diagram showing one example of an ultrasonic probe cap of the first embodiment in which a plurality of small transducers are arranged in a mosaic-like pattern on the inside of the cap.
Figure 3:
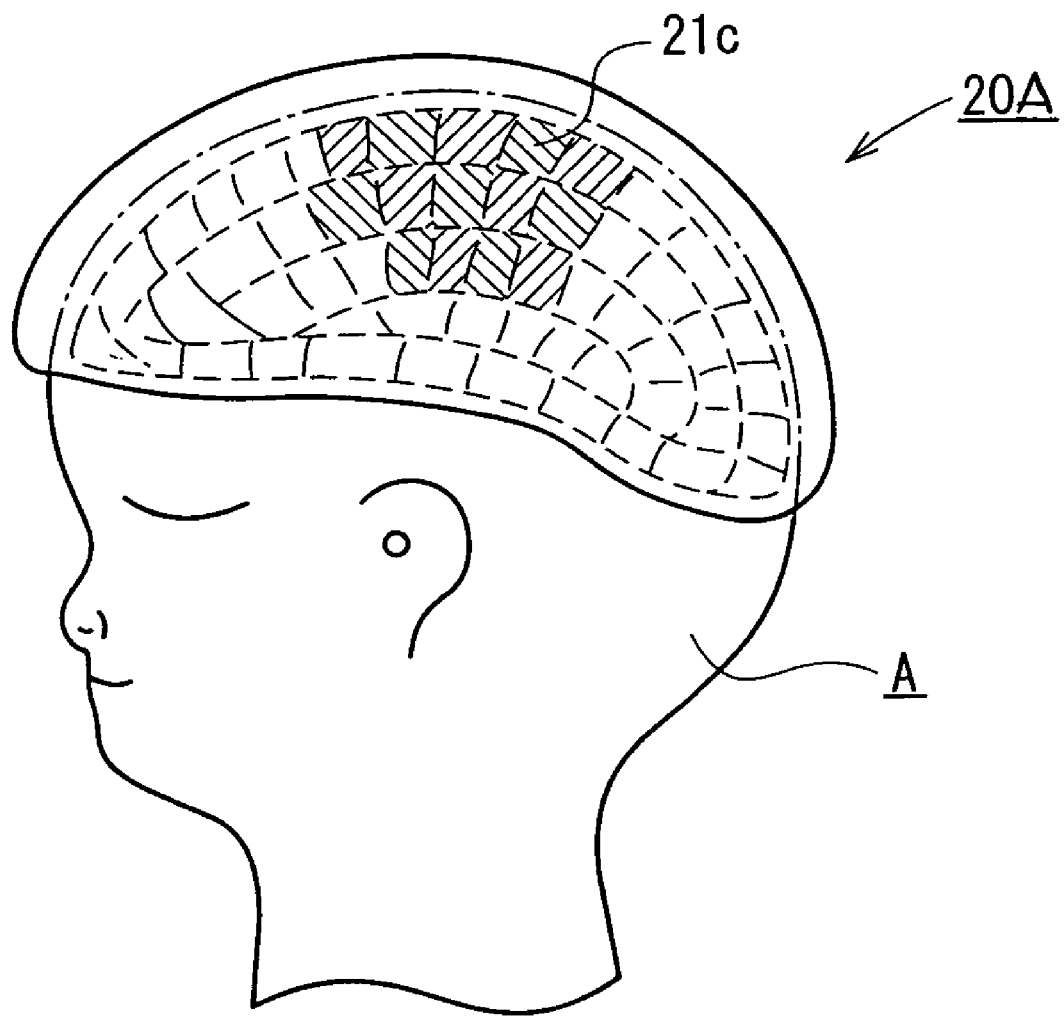
FIG. 3 is a diagram showing another example of the first embodiment of an ultrasonic probe cap in which a plurality of small transducers are arranged in a mosaic-like pattern on the inside of the cap.

FIG. 2 and FIG. 3 are diagrams showing the first embodiment of the ultrasonic probe cap 20A that is constructed by arranging the plurality of ultrasonic transducers 21 each being a lamination of the PVDF films on the inside of the cap.

FIG. 2 shows the ultrasonic probe cap 20A of the first example of the first embodiment. This is the example in which near the parietal region whose bone is thick, a belt-shaped transducer 21a of a center frequency of, for example, 200 kHz is disposed in the ultrasonic probe cap 20A, whereas in the temporal region whose bone thickness is thin, a belt-shaped transducer 21b of a center frequency higher than that of the former, for example, 500 kHz is disposed, considering that the bone thickness of human cranial bone is thick near the parietal region and is thin in the temporal region. Note that in this embodiment, although the ultrasonic transducers 21 are two, i.e., the belt-shaped transducers 21a and 21b, the number of them may be one, or three or more.

FIG. 3 shows the ultrasonic probe cap 20A of the second example of the first embodiment. This is the example in which a plurality of ultrasonic transducers 21c each of which is smaller than that shown in FIG. 2 are arranged in a mosaic-like pattern. The ultrasonic probe cap 20A shall be so configured that natural frequencies of the transducers 21c are mutually different and a size of each ultrasonic transducer 21c is selected and determined not to be $\frac{1}{4}\lambda$ ($\lambda$: natural vibration wavelength) multiplied by an integer in order to avoid resonance.

Although in the first and second examples, the ultrasonic transducer is made up of the PVDF film, instead of this, the ultrasonic transducer may be made up of a PZT ceramic and arranged on the inside of the cap-like holding member. Although the PZT ceramics are hard materials, it becomes possible to bring it into tight contact with the head by reducing the length and width in the case of a belt-shaped transducer. In addition, in the case of transducers arranged in a mosaic-like pattern, it becomes possible to bring it into tight contact with the head by reducing the size of each transducer.

Moreover, the ultrasonic probe cap 20A described above is constructed to cover a part or the whole of the head of the patient under therapy A.

From among the belt-shaped transducer 21a disposed near the parietal region, the belt-shaped transducer 21b disposed in the temporal region, and a plurality of transducers 21c arranged in a mosaic-like pattern, one or plurality of ultrasonic transducers located near the embolic site are selected and activated through the switching circuit 33 by an operation of the display operation unit 40 of the control device 30 that will be described later. Hereafter, there is a case where the belt-shaped transducers 21a, 21b and the plurality of transducers 21c arranged in a mosaic-like pattern are called ultrasonic transducers 21a-21n collectively to give explanation.

When the high frequency current is supplied to the ultrasonic transducers 21a-21n arranged in the ultrasonic probe cap 20A, they will vibrate and generate heat. Moreover, the cranial bone of the patient under therapy A to which the ultrasonic wave is irradiated from the ultrasonic probe cap 20A generates heat because of absorption of the ultrasonic vibration. Since such heat generation of the ultrasonic transducer and heat generation of the cranial bone have adverse effects on the brain tissue, they need to be cooled. For this purpose, the cooling device 50 (see FIG. 4) is disposed between the ultrasonic transducer of the ultrasonic probe cap 20A and a surface of the skin of the head of the patient under therapy A, and is controlled based on a detected signal of the temperature sensor 25 (see FIG. 4) provided on the ultrasonic probe cap 20A. This will be explained in detail later.

Figure 4:
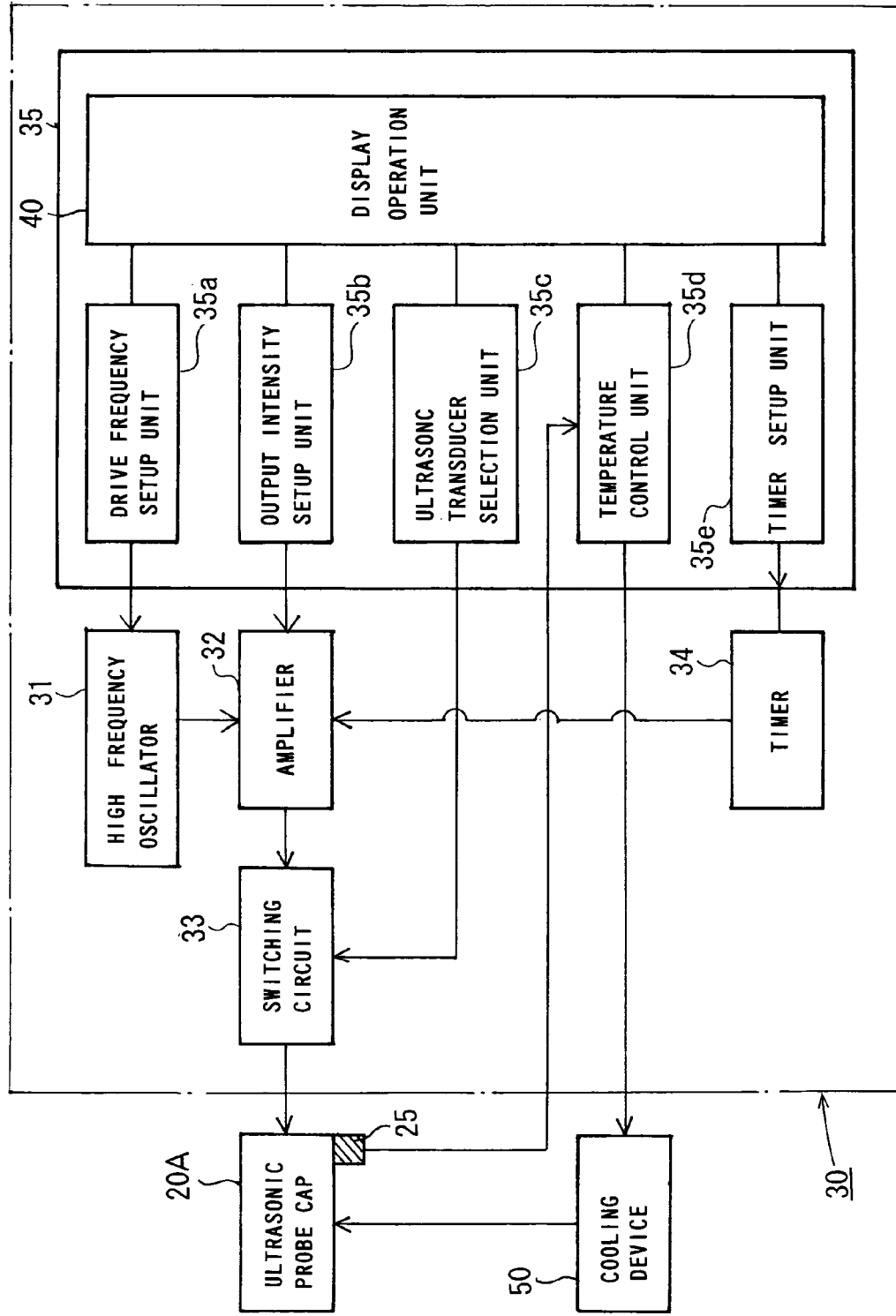
FIG. 4 is a block diagram explaining a configuration of a control device.

FIG. 4 is a block diagram explaining a configuration of the control device 30. The control device 30 consists of the high frequency oscillator 31 that outputs the high frequency current for activating the ultrasonic transducer, the amplifier 32, the switching circuit 33 that select one or plurality of ultrasonic transducers to be excited and supplies a high-frequency current to it, a timer 34, and the control unit 35, and the display operation unit 40 is attached to the control unit 35.

The control unit 35 is made up of a CPU, more specifically, having a drive frequency setup unit 35a of the ultrasonic transducer, an output intensity setup unit 35b, an ultrasonic transducer selection unit 35c, a temperature control unit 35d, and a timer setup unit 35e, and controls the whole apparatus. Based on signals inputted from the dials and the switches of the display operation unit 40, the drive frequency setup unit 35a, the output intensity setup unit 35b, the ultrasonic transducer selection unit 35c, and the timer setup unit 35e perform setup of the drive frequency, setup of the output intensity, selection of an ultrasonic transducer, setup of an irradiation time of the timer, etc., respectively.

When the set-up time lapses, the timer 34 outputs an interrupting signal to the amplifier 32 (or the high frequency oscillator 31) to effect stopping of irradiation of the ultrasonic wave.

Figure 5:
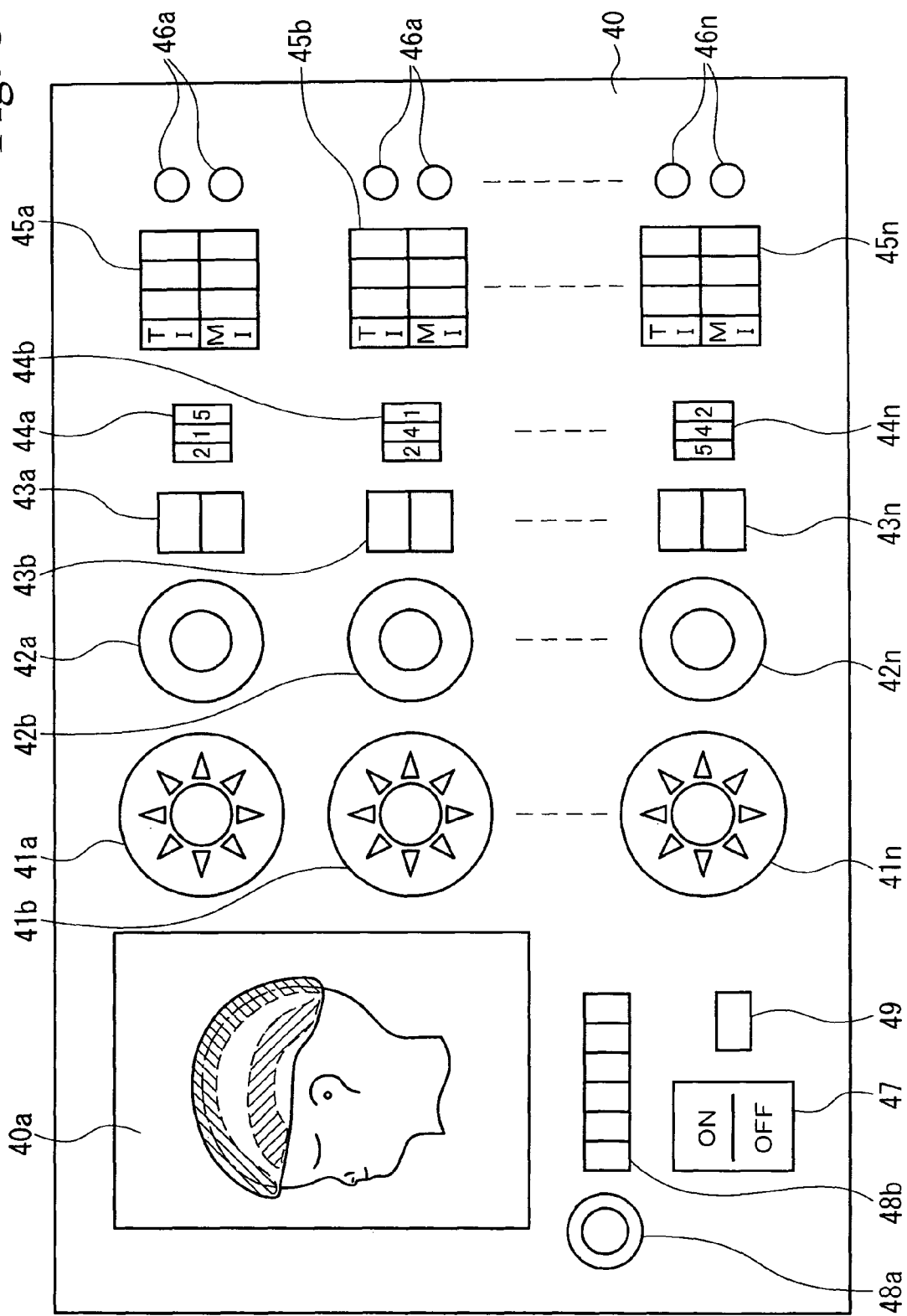
FIG. 5 is a diagram explaining one example of a display operation unit of the control device.

FIG. 5 is a diagram showing one example of the display operation unit 40 of the control device 30, in which, corresponding to the ultrasonic transducers 21a-21n arranged in the ultrasonic probe cap 20A, the following are arranged: A plurality of dials 41a-41n each for setting up the frequency or voltage of the high frequency current to be supplied; a plurality of dials 42a-42n each for setting up the output intensity of the high frequency current to be supplied; switches 43a-43n for selecting an ultrasonic transducer to be excited; displays 44a-44n for displaying the intensities (W/cm2) of the ultrasonic waves being irradiated; displays 45a-45n for displaying the respective thermal index TI values and mechanical index MI values that will be described later; alarm lamps 46a-46n; an ON/OFF switch 47 for starting and stopping irradiation of the ultrasonic wave, a timer setup dial 48a for setting up a time on the timer 34 for measuring an irradiation time; a timer display 48b; a power supply lamp 49; etc.

In addition to them, a display 40a for displaying rough positions of the ultrasonic transducers 21a-21n arranged on the inside of the ultrasonic probe cap 20A etc. may be provided in the display operation unit 40.

Figure 6:
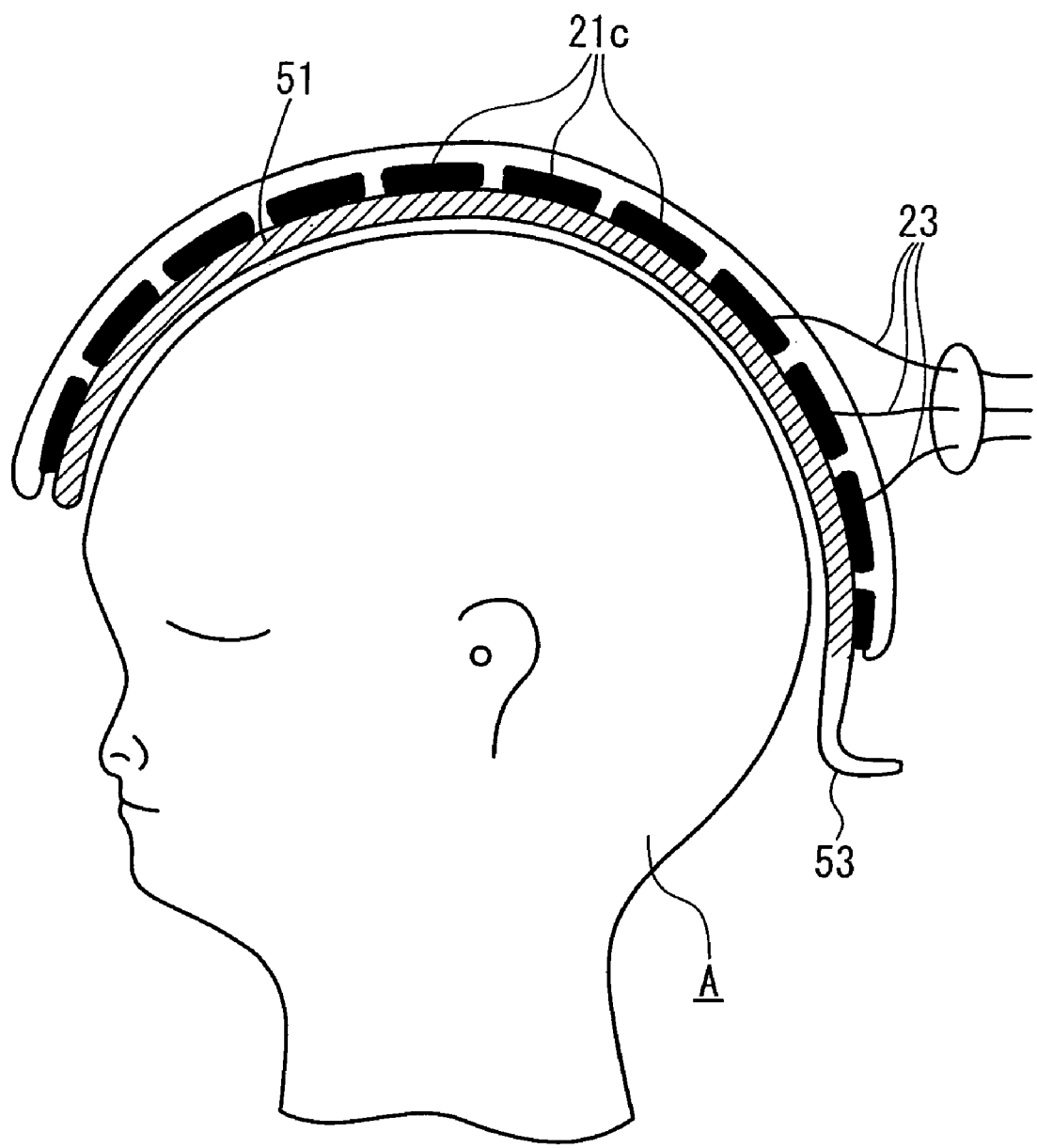
FIG. 6 is a diagram explaining the ultrasonic probe cap and a wearing state of a cooling jacket.

As the cooling device 50, a cooling jacket 51 is used in this embodiment. FIG. 6 is a diagram for explaining a wearing state of the ultrasonic probe cap 20A and the cooling jacket 51. The plurality of transducers 21c arranged in a mosaic-like pattern in the ultrasonic probe cap 20A are shown in this figure. However, in the case of the belt-shaped transducers 21a, 21b, the wearing state is the same. Incidentally, the ultrasonic probe cap 20A and the cooling jacket 51 are shown as in their cross-sections. The reference numeral 23 shows wiring for feeding electric power to the ultrasonic transducers and the numeral 53 shows water supply pipe.

The cooling jacket 51 is disposed between the ultrasonic transducers 21a-21n and the skin surface of the head of the patient under therapy A to bring the ultrasonic transducers 21a-21n into tight contact with the skin surface of the head of the patient under therapy A. For this reason, the cooling jacket 51 is made of a flexible and tough synthetic resin film. The apparatus is so configured that cold water is circulated to the cooling jacket 51 from the circulating pump 52 through the water supply pipe 53 (see FIG. 1) to cool the ultrasonic transducers 21a-21n and cool the head of the patient under therapy A through the skin surface. Its implementation itself shall be based on known means.

Moreover, the temperature sensor 25 (see FIG. 4) shall be provided for each of the ultrasonic transducers 21a-21n or for each of predetermined areas on a part of the ultrasonic probe cap 20A that contacts the head of the patient under therapy A, and shall be configured to display a warning when the detected temperature increases from a temperature before the start of ultrasonic irradiation by 1.5° C. or more or when it exceeds 38° C. Its implementation shall be done by known means.

Alternatively, the cooling means may be as follows: A Peltier effect element made up of a metal thin film capable of decreasing temperature by the Peltier effect is stuck on the surfaces (surfaces facing respective portions of the skin surface of the head of the patient under therapy A) of the ultrasonic transducers 21a-21n arranged on the inside of the ultrasonic probe cap 20A and they are each cooled by the Peltier effect element. Such a metal thin film does not work as a special drawback against propagation of the ultrasonic wave irradiated from the ultrasonic transducer. This structure can also cool the ultrasonic transducers and the head of the patient under therapy A through the skin surface.

As the cooling means, a cooling jacket made of a tough synthetic resin film and filled with cooling jelly may be used instead of the above mentioned. In this case, the cooling jacket is cooled at a predetermined low temperature in advance and, at the time of ultrasonic irradiation therapy, is disposed between the ultrasonic transducers 21a-21c of the ultrasonic probe cap 20A and the skin surface of the head of the patient under therapy A. Adoption of this configuration eliminates necessity of the circulating pump and the water supply pipe or a feeder system to the Peltier elements etc.

Figure 7:
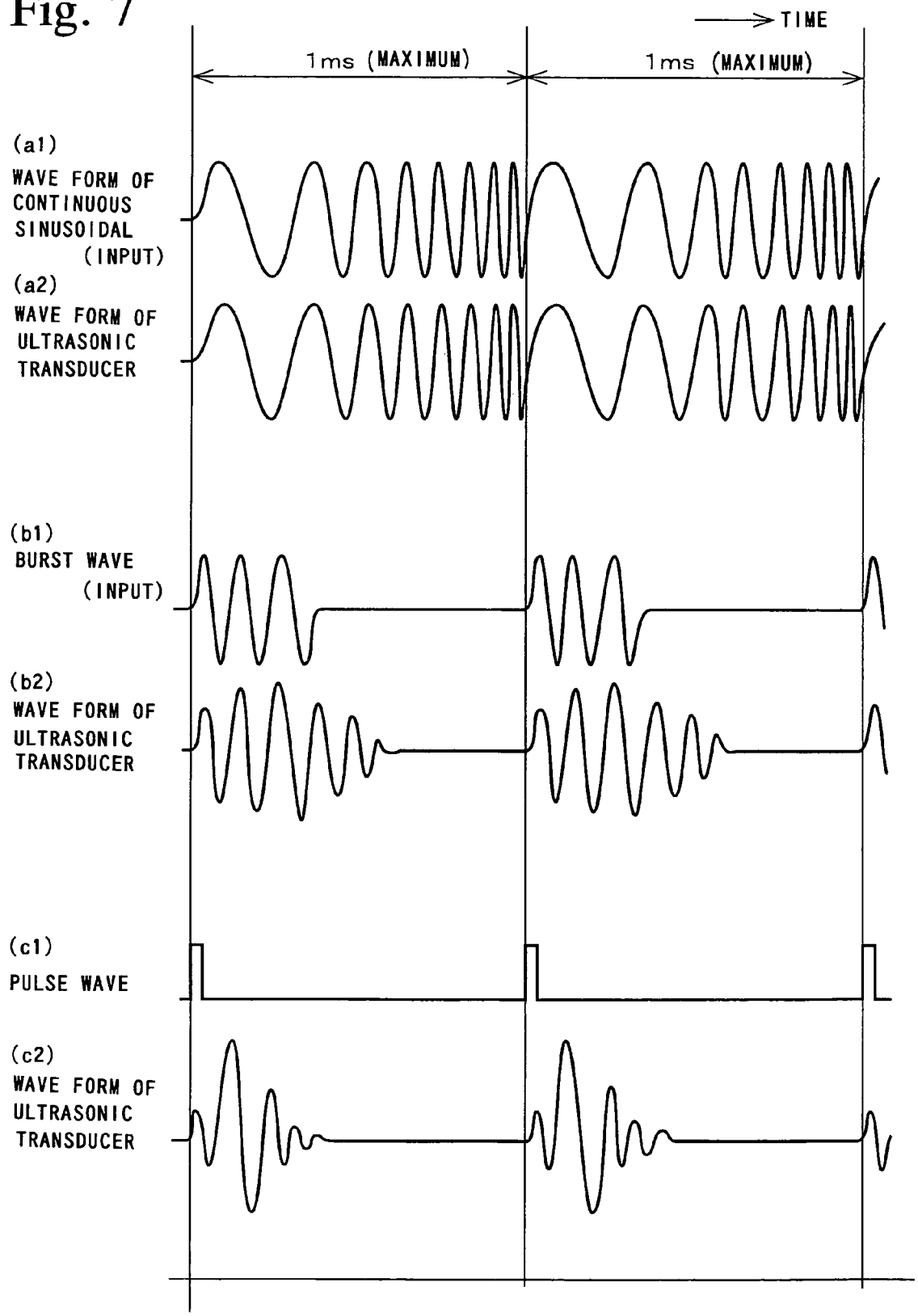
FIG. 7 is a diagram explaining waveforms of high frequency currents outputted from a high frequency oscillator.

The high frequency oscillator 31 for activating the ultrasonic transducers 21a-21n will be explained. FIG. 7 is a diagram explaining waveforms of high frequency signals outputted from the high frequency oscillator 31; used is a continuous sinusoidal wave shown by (a1) of FIG. 7, a burst wave (intermitting sinusoidal wave for a repetition cycle of a predetermined time) shown by (b1) of FIG. 7, or a pulse wave shown by (c1) of FIG. 7.

In the case of the continuous sinusoidal wave, as shown by (a1) of FIG. 7, it is frequency modulated so that its frequency may be varied periodically. This is done because if the ultrasonic wave is irradiated continuously from the outside of the cranial bone at the same frequency, there is a risk that an ultrasonic beam irradiated into the inside of the cranial bone from the outside through one side of the cranial bone is reflected on the internal surface of the cranial bone on the other side, which causes a local increase of acoustic pressure leading to breeding and damages nerve cells. In the case of the continuous sinusoidal wave, formation of the standing wave by interference of the irradiated beam and the reflected beam can be avoided by performing frequency modulation.

A fundamental frequency of the continuous sinusoidal wave shall be 2 MHz or less, and an appropriate frequency shift width is determined. A frequency modulation speed shall be 1 Hz/ms, i.e., 1 kHz/s or more. This is determined from a critical time during which no acoustic cavitation occurs even if ultrasonic irradiation produces a standing wave in the cranium.

When the ultrasonic transducer is activated by the continuous sinusoidal wave shown by (a1) of FIG. 7, ultrasonic waveform as shown by (a2) of FIG. 7 will be oscillated and irradiates the ultrasonic vibration.

Figure 8:
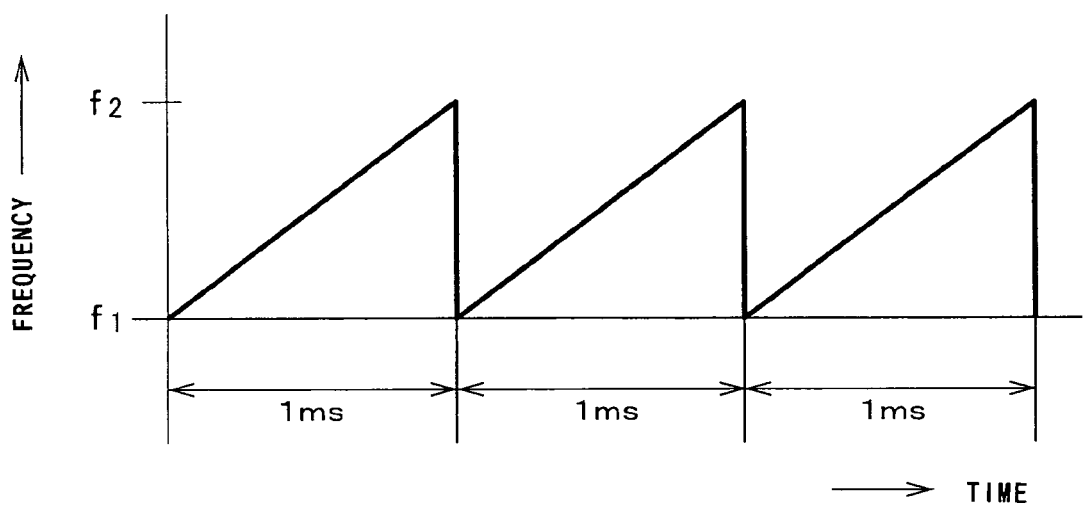
FIG. 8 is a diagram explaining one example of a state of a frequency-modulated continuous sinusoidal wave.

FIG. 8 is a diagram explaining one example of a state of a frequency-modulated continuous sinusoidal wave. setting a unit time to 1 ms, namely, setting a repetition cycle to 1 ms or less, the frequency varies from f1 to f2 during this unit time. In the next unit time, the varies from f1 to f2 after returning back to f1 again.

In the case of the burst wave, as shown by (b1) of FIG. 7, formation of a standing wave in the cranium can be avoided by setting the fundamental frequency to 2 MHz or less and setting a duration to 1 ms or less. When the ultrasonic transducer is activated by a burst wave shown by (b1) of FIG. 7, the ultrasonic waveform as shown by (b2) of FIG. 7 will be oscillated and irradiates the ultrasonic vibration.

In the case of the pulse wave, as shown by (c1) of FIG. 7, the fundamental frequency shall be 2 MHz or less and a duration shall be 1 ms or less, whereby formation of a standing wave inside the cranium can be avoided. When the ultrasonic transducer is activated by a pulse wave shown by (c1) of FIG. 7, ultrasonic waveform as shown by (c2) of FIG. 7 will be oscillated and irradiates the ultrasonic vibration.

The mean output intensity of the high frequency signal outputted from the high frequency oscillator 31 shall be 1 W/cm2 or less in the cases of the continuous sinusoidal wave, the burst wave, and the pulse wave.

The switching circuit 33 will be explained. The switching circuit 33 is an ON/OFF circuit that selects an ultrasonic transducer (ultrasonic transducer to be excited) suitable to irradiate the ultrasonic wave onto the targeted embolic site from among the ultrasonic transducers 21a-21c arranged on the inside of the ultrasonic probe cap 20A described above and supplies it with a high frequency signal, being operating under control of the control unit 35. The switching circuit itself is made up of a switching device, such as a known semiconductor device.

Here, a relation of the oscillation frequency of the high frequency oscillator, i.e., the frequency of ultrasonic vibration versus the intensity and a relation of the temperature rise of biomedical tissue versus the intensity of ultrasonic vibration will be explained.

According to experiments, a thrombolysis effect is higher with lowering frequency provided that the intensity of ultrasonic vibration is the same. However, if the intensity of ultrasonic vibration becomes high, acoustic cavitation (cavity) will be generated in biomedical tissue, and will destroy cellular tissue. Let a critical limit of the ultrasonic vibration at which acoustic cavitation is generated be a mechanical index MI=1.0, and hereafter the intensity of ultrasonic vibration will be indicated by a value of the mechanical index MI.

Since cellular tissue will be destroyed at MI=1.0, here, the mechanical index must be multiplied by an appropriate safety factor, in this embodiment, ¼. So, the permissible safety intensity of ultrasonic vibration is set to MI=0.25.

A critical frequency (lower limit) of available ultrasonic vibration frequencies at which MI=0.25 stands is calculated by a Formula adopting a safety standard value 0.72 W/cm2 of US Food and Drug Administration (FDA) for outputs of the ultrasonic diagnostic apparatuses that took into consideration safety to biomedical tissue as a maximum irradiation power. The calculation gives frequency f=270 kHz.

The higher the intensity of ultrasonic vibration being irradiated, the higher the critical frequency becomes. If the intensity of ultrasonic vibration is lowered, the critical frequency can be extended to lower frequencies.

In addition, the temperature rise of biomedical tissue has a relation with the intensity and frequency of ultrasonic vibration; the temperature rises higher with increasing intensity and with increasing frequency of ultrasonic vibration, respectively. Since an effect of the temperature rise on biomedical tissue can be expressed by a difference from a normal temperature of biomedical tissue, an index indicating a difference of temperature that is given 0° C. for a normal temperature difference of biomedical tissue is defined as a thermal index TI, and any temperature difference is expressed by the index TI value.

Figure 9:
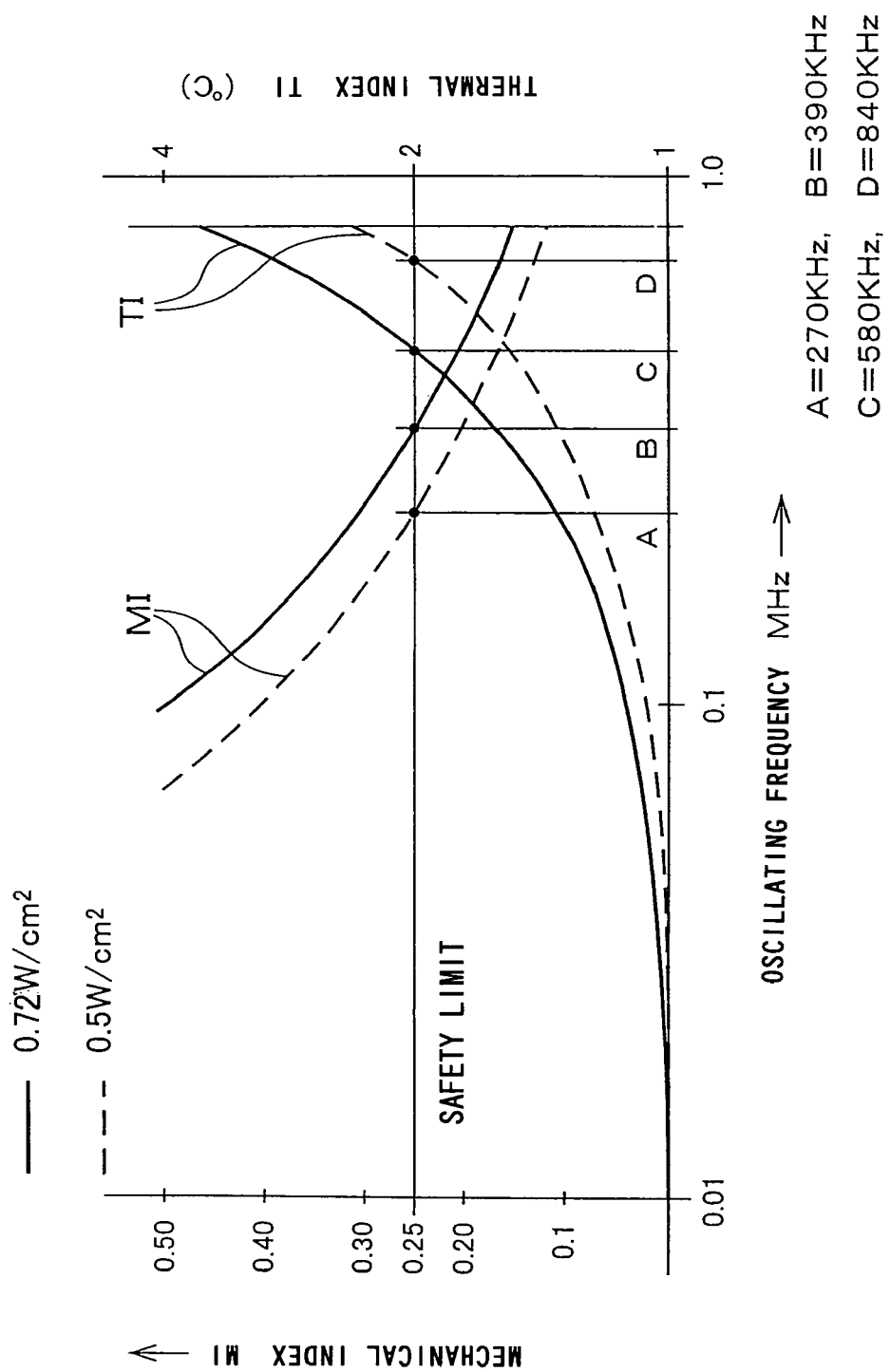
FIG. 9 is a diagram showing relations of a mechanical index MI and a thermal index TI versus the frequency for two different intensities of ultrasonic wave.

FIG. 9 is a diagram showing results of having checked the relation of the mechanical index MI and the thermal index TI versus the frequency of ultrasonic wave for different intensities of ultrasonic wave. The horizontal axis represents the frequency (MHz) of ultrasonic vibration and the vertical axis represents the mechanical index MI and the thermal index TI (° C.) for the case of an ultrasonic wave output of 0.72 W/cm2 (safety standard value) and for the case of 0.5 W/cm2, which is lower than the above.

The "safety limit" of FIG. 9 shows permissible safety intensity MI=0.25 of ultrasonic vibration and temperature-rise tolerance limit value TI=2.0 of biomedical tissue.

As is clear from this figure, provided that the output of the ultrasonic wave is constant (0.72 W/cm2 or 0.5 W/cm2), it is found that the mechanical index MI, i.e., the intensity index of ultrasonic vibration, becomes lower with increasing frequency, whereas the thermal index TI, i.e., the temperature index indicating an effect of temperature on biomedical tissue, becomes higher with increasing frequency.

It has been found that an available frequency range considering "safety limit" becomes a range of 390 kHz to 580 kHz in the case of an ultrasonic output of 0.72 W/cm2, and a range of 270 kHz to 840 kHz in the case of an ultrasonic output of 0.5 W/cm2. Therefore, in consideration of a variation width of ultrasonic output etc., an available frequency range becomes a range of 250 kHz to 850 kHz.

Next, how to use the ultrasonic cerebral infarction therapeutic apparatus will be explained. First, a site of cerebral infarction of the patient under therapy, i.e., a position of the targeted embolic site is specified by the X-ray contrastradiography or the digital subtraction elimination angiography (DSA) as a preparatory step, and an optimal thrombolytic agent is prepared.

Next, the operator of the apparatus selects the ultrasonic probe cap 20A suitable to irradiate the ultrasonic wave onto a position of a specified embolic site and sets it on the head of the patient under therapy. At this time, the cooling jacket 51 is disposed between the ultrasonic transducers 21a-21n arranged in the ultrasonic probe cap 20A, connected with the circulating pump 52, and the wiring 23 for supplying electric power to the ultrasonic transducers 21a-21n is connected with the control device 30.

The operator operates the switches 43a-43n of the display operation unit 40, selects an ultrasonic transducer suitable to irradiate the ultrasonic wave onto the position of the targeted embolic site, sets up a frequency or voltage of the high frequency current supplied to the ultrasonic transducer by operating the dials 41a-41n, and sets up an output intensity (amplification degree) of the high frequency current to be supplied by operating the dials 42a-42n.

A CPU in the control device 30 calculates the intensity (W/cm2) of the ultrasonic wave to be irradiated based on selection information about the ultrasonic transducer to be excited, information about the frequency or voltage of the high frequency current to be supplied, and information about the amplification degree of the high frequency current, and displays them in the displays 44a-44n. Moreover, the CPU calculates the thermal index value (TI value) and the mechanical index value (MI value) based on the selected information, and displays them in the displays 45a-45n. Then, the CPU determines whether the calculated TI value and MI value are each within a range of tolerance limit value. If any one of the two is out of the range, the CPU turns on the alarm lamps 46a-46n to issue a warning. If the warning indication is made, the operator of the apparatus alters the frequency or voltage of the high frequency current and the amplification degree of the high frequency current so that the intensity of the ultrasonic wave being irradiated may fall within the range of the tolerance limit value. Finally, the operator sets up an ultrasonic irradiation time in the timer 34 by operating the timer setup dial 48a.

In this way, the ultrasonic transducer to be excited is selected, the frequency or voltage and the amplification degree of the high frequency current to be supplied, are set up, and the ultrasonic irradiation time is set up in the timer. The operator checks completion of preparation.

Intravenous infusion of the optimal thrombolytic agent by drip is started, and the switch 47 of the display operation unit 40 is turned ON. With the start of irradiation of the ultrasonic wave to the targeted embolic site, a switch of the circulating pump 52 is turned ON and supply of cold water to the cooling jacket 51 is started by activation of the circulating pump 52, and the timer 34 starts to measure a time of the ultrasonic irradiation time.

The operator checks the ultrasonic irradiation time displayed in the timer display 48b and, if a predetermined irradiation time has lapsed, turns OFF the switch 47 to finish the ultrasonic irradiation. Incidentally, the timer 34 shall be given a predetermined irradiation time in advance and start to measure when the switch 47 is turned ON. The switch 47 may be configured to automatically turn OFF when a predetermined irradiation time has lapsed.

Moreover, it is recommended that, after the end of ultrasonic irradiation, when there occurs any trouble in which the TI value or MI value exceeds the tolerance limit value, or when a temperature inside the ultrasonic probe cap 20A detected by the temperature sensor 25 or a temperature of water circulating the cooling jacket 51 rises abnormally, or in other events, the timer be configured to raise an alarm and stop the ultrasonic irradiation.

Next, the ultrasonic probe pad 20B that is the second embodiment of the ultrasonic irradiation device 20 will be explained.

The ultrasonic probe pad 20B is a pad of the ultrasonic transducer having flexibility that is made up of a polyvinylidene fluoride (PVDF) film as a row material so that ultrasonic transducers can be attached to a part or the whole of the head of the patient under therapy A.

PVDF is a material having an electromechanical transfer characteristic (piezo-electric characteristic), and the thickness of its film determines an efficient drive frequency. Based on this fact, in order to match the ultrasonic probe pad 20B to a comparatively low frequency to be used, positive and negative electrodes are formed on the both sides of the PVDF film by means of vapor deposition etc. and necessary number of the films are laminated to constitute a pad of the ultrasonic transducer according to the drive frequency.

Figure 10:
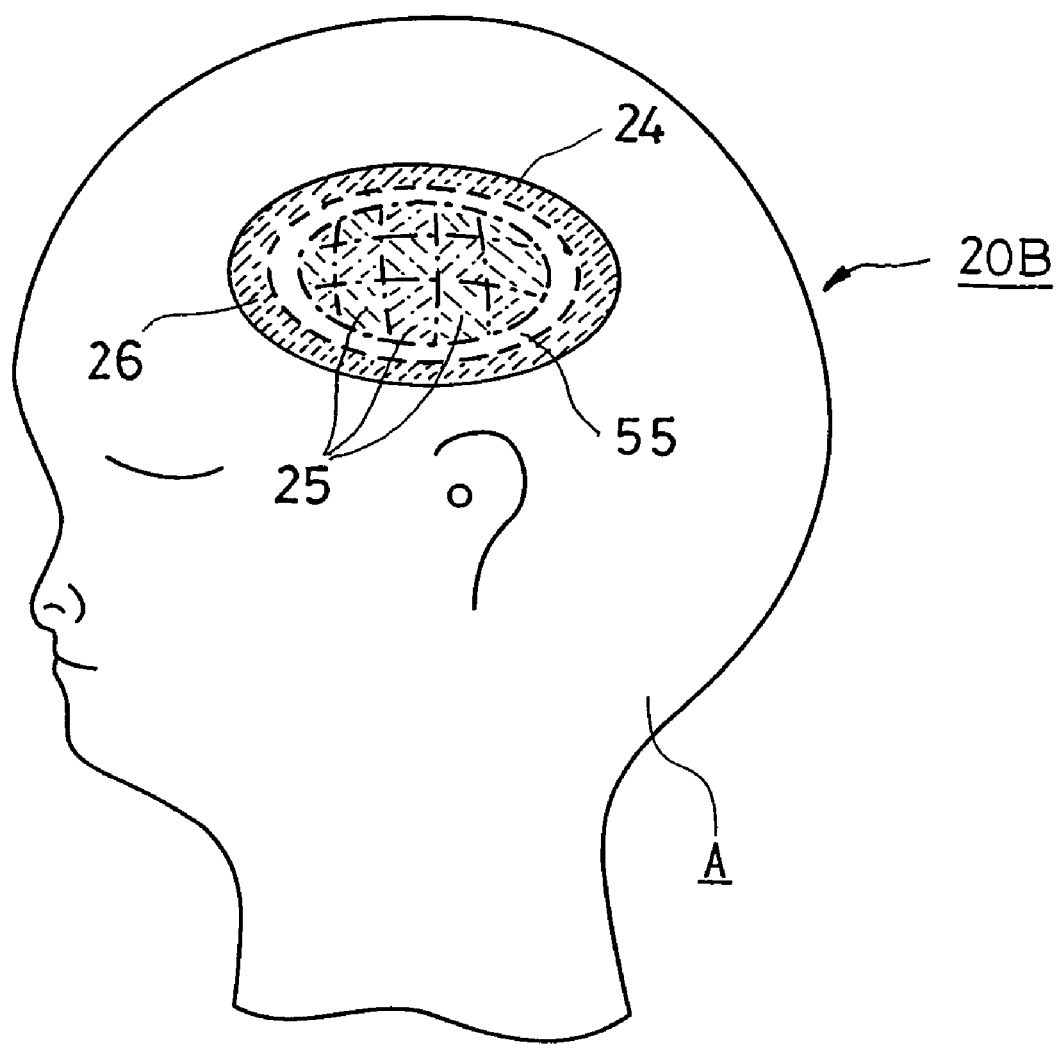
FIG. 10 is a diagram explaining a construction of an ultrasonic probe pad and a wearing state of a cooling jacket of a second embodiment.

FIG. 10 is a diagram explaining the ultrasonic probe pad 20B of the second embodiment and a wearing state of the cooling jacket. Positive and negative electrodes are formed on the both sides of the PVDF film by means of vapor deposition etc. and a predetermined number of the films are laminated according to the drive frequency to finish a PVDF film 24 on which the one or the plurality of ultrasonic transducers 25 are formed. An adhesive plane 26 to which an adhesive is applied is provided to a fringe of the PVDF film 24 except for a portion of the electrode of the ultrasonic transducer 25 to complete the ultrasonic probe pad 20B. The adhesive plane 26 is a member to allow the ultrasonic probe pad 20B to be stuck directly to the head of the patient under therapy A. FIG. 10 shows a state where it is stuck to the temporal region of the patient under therapy A.

Although the ultrasonic transducer 25 is made up of the PVDF film in the ultrasonic probe pad 20B of the second embodiment, the following construction may be adopted. The ultrasonic transducer 25 is made up of a PZT ceramic instead of the PVDF film, and the ultrasonic probe pad 20B is prepared with a flexible material whose fringe, acting as the adhesive plane 26, is coated with an adhesive and the ultrasonic transducer 25 of the PZT ceramic is stuck to a portion other than the adhesive plane 26. Although PZT ceramics are hard materials, it becomes possible to bring such an ultrasonic probe pad into tight contact with the head by reducing the size of the transducers.

Moreover, the ultrasonic probe pad 20B is constructed to cover a part or the whole of the head of the patient under therapy A. When setting the ultrasonic probe pad 20B on the head of the patient under therapy A, first, a position of the targeted embolic site is pinpointed, the ultrasonic probe pad 20B of an appropriate size is selected, and a position at which the ultrasonic probe pad 20B is attached is determined. Next, a cooling jacket 55 with cooling jelly filled therein is arranged so as to be under the ultrasonic probe pad 20B, and the ultrasonic probe pad 20B is disposed on the cooling jacket 55. The adhesive plane 26 provided on the fringe of the ultrasonic probe pad 20B is directly stuck on the skin surface of the head of the patient under therapy A, and the ultrasonic probe pad 20B is fixed.

Although in this embodiment the cooling jacket 55 with cooling jelly filled therein is used as a cooling device, the cooling device is not limited to this. It is natural that other cooling device explained in the first embodiment can be used. Activating the ultrasonic probe pad 20B is the same as described in the first embodiment, and accordingly its explanation will be omitted in this embodiment.

INDUSTRIAL APPLICABILITY

The ultrasonic cerebral infarction therapeutic apparatus of this invention is an apparatus that dissolves thrombus responsible for cerebral infarction of the patient under therapy by irradiating the ultrasonic wave onto the embolic site.

What is claimed is:

1. An ultrasonic cerebral infarction therapeutic apparatus that dissolves thrombus by irradiating an ultrasonic wave through the cranium to an embolic site of the cerebral blood vessel in the cranium, comprising:
    an ultrasonic irradiation device equipped with one or a plurality of ultrasonic transducers constructed to cover a part or the whole of the head of a patient under therapy;
    a high frequency oscillator that supplies a high frequency signal for activating the ultrasonic transducers;
    a switching device for selecting one or several ultrasonic transducers that are suitable to irradiate the ultrasonic wave toward the embolic site from among the one or the plurality of ultrasonic transducers; and
    a control device for supplying a high frequency signal outputted from the high frequency oscillator to the one or the plurality of ultrasonic transducers selected by the switching device;
    wherein the high frequency signal supplied from the high frequency oscillator is selected from one of following waves:
    (1) a frequency-modulated continuous sinusoidal wave that does not maintain the same frequency for a time longer than 1 ms,
    (2) a burst wave such that each one of signals constituting the burst wave has an excitation duration of less than 1 ms,
    (3) a pulse wave such that each one of pulses constituting the pulse wave has an excitation duration of less than 1 ms, and
    wherein repetition of said excitation duration period is 1 ms or less.

2. The ultrasonic cerebral infarction therapeutic apparatus according to claim 1,
    wherein the ultrasonic irradiation device is a cap-like ultrasonic irradiation device constructed by arranging the one or the plurality of ultrasonic transducers each made by laminating a polyvinylidene fluoride (PVDF) film on the inside of a cap-like holding member made up of a flexible material so as to cover a part or the whole of the head of the patient under therapy.

3. The ultrasonic cerebral infarction therapeutic apparatus according to claim 1,
    wherein the ultrasonic irradiation device is a pad-like ultrasonic irradiation device constructed with a polyvinylidene fluoride (PVDF) film on which one or a plurality of ultrasonic transducers are formed and that is made up of a flexible material whose fringe is provided with an adhesive plane to which an adhesive agent is applied so as to be brought into tight contact with a part or the whole of the head of the patient under therapy.

4. The ultrasonic cerebral infarction therapeutic apparatus according to claim 1,
    wherein the ultrasonic irradiation device is a cap-like ultrasonic irradiation device constructed by arranging the one or the plurality of ultrasonic transducers each made by laminating a PZT ceramic on the inside of a cap-like holding member made up of a flexible material so as to cover a part or the whole of the head of the patient under therapy.

5. The ultrasonic cerebral infarction therapeutic apparatus according to claim 1,
    wherein the ultrasonic irradiation device is a pad-like ultrasonic irradiation device constructed by arranging the one or the plurality of ultrasonic transducers each made up of a PZT ceramic on the inside of a flexible material whose fringe is provided with an adhesive plane to which an adhesive agent is applied so as to be brought into tight contact with a part or the whole of the head of the patient under therapy.

6. The ultrasonic cerebral infarction therapeutic apparatus according to claim 1,
    wherein continuous sinusoidal waves supplied to the plurality of ultrasonic transducers are mutually different in phase.

7. The ultrasonic cerebral infarction therapeutic apparatus according to claim 1,
    wherein a mean output intensity of the high frequency signal supplied from the high frequency oscillator is 1 W/cm2 or less.

8. The ultrasonic cerebral infarction therapeutic apparatus according to claim 1,
    wherein the control device has a display operation unit that adjusts the frequency or voltage and the amplification degree of the high frequency signal supplied to the one or the plurality of ultrasonic transducers selected by the switching device and displays the intensity and the irradiation time of the ultrasonic wave being irradiated.

9. The ultrasonic cerebral infarction therapeutic apparatus according to claim 1,
    wherein the ultrasonic irradiation device is provided with a temperature sensor for detecting temperatures of the head of the patient under therapy and of the ultrasonic transducer, and the temperatures are monitored by the control device.

10. The ultrasonic cerebral infarction therapeutic apparatus according to claim 1, further comprising a cooling device disposed between the ultrasonic irradiation device and the skin of the head of the patient under therapy,
    wherein the cooling device closely contacts with the skin of the head.

11. The ultrasonic cerebral infarction therapeutic apparatus according to claim 10,
    wherein the cooling device is a flexible cooling jacket through which cold water circulates.

12. The ultrasonic cerebral infarction therapeutic apparatus according to claim 10,
    wherein the cooling device is a cooling device constructed by sticking down a Peltier element made up of a metal thin film having the Peltier effect on the surface of the ultrasonic transducer.

13. The ultrasonic cerebral infarction therapeutic apparatus according to claim 10,
    wherein the cooling device is a flexible cooling jacket with cooling jelly filled therein.

* * * * *